United States Patent [19]

Ishihara et al.

[11] 4,276,286

[45] * Jun. 30, 1981

[54] PROCESS FOR DECREASING AMMONIA CONCENTRATION IN DOMESTIC ANIMALS OR FOWLS

[75] Inventors: Eisuke Ishihara, Shizuoka; Hiroshi Yonehara, Tokyo; Katsuyuki Akasaki, Shimizu; Masao Minowa; Katsumi Kobayashi, both of Shizuoka, all of Japan

[73] Assignee: Kumiai Chemical Industry Co., Ltd., Tokyo, Japan

[*] Notice: The portion of the term of this patent subsequent to Jan. 6, 1988, has been disclaimed.

[21] Appl. No.: 112,218

[22] Filed: Jan. 15, 1980

Related U.S. Application Data

[63] Continuation-in-part of Ser. No. 32,253, Apr. 23, 1979, which is a continuation of Ser. No. 830,773, Sep. 6, 1977, abandoned, which is a continuation of Ser. No. 736,523, Oct. 28, 1976, abandoned, which is a continuation-in-part of Ser. No. 681,198, Apr. 28, 1976, abandoned.

[30] Foreign Application Priority Data

Oct. 28, 1975 [JP]  Japan ............................ 50/128910

[51] Int. Cl.$^3$ .............................................. A61K 35/00
[52] U.S. Cl. ..................................................... 424/117
[58] Field of Search .......................................... 424/117

[56] References Cited

PUBLICATIONS

The Journal of Antibiotics, vol. XXIII, No. 5, 231–237.

*Primary Examiner*—Frederick E. Waddell
*Attorney, Agent, or Firm*—Stevens, Davis, Miller & Mosher

[57] ABSTRACT

The invention relates to a process for decreasing the ammonia concentration in the interior of the body of domestic animals and fowls, thereby maintaining said animals and fowls in physiologically good condition and decreasing the ammonia concentration in the excrement thereof to decrease the offensive odor generated from the excrement. This is carried out by giving them the antibiotic multhiomycin in the feed or the drinking water containing multhiomycin.

4 Claims, 1 Drawing Figure

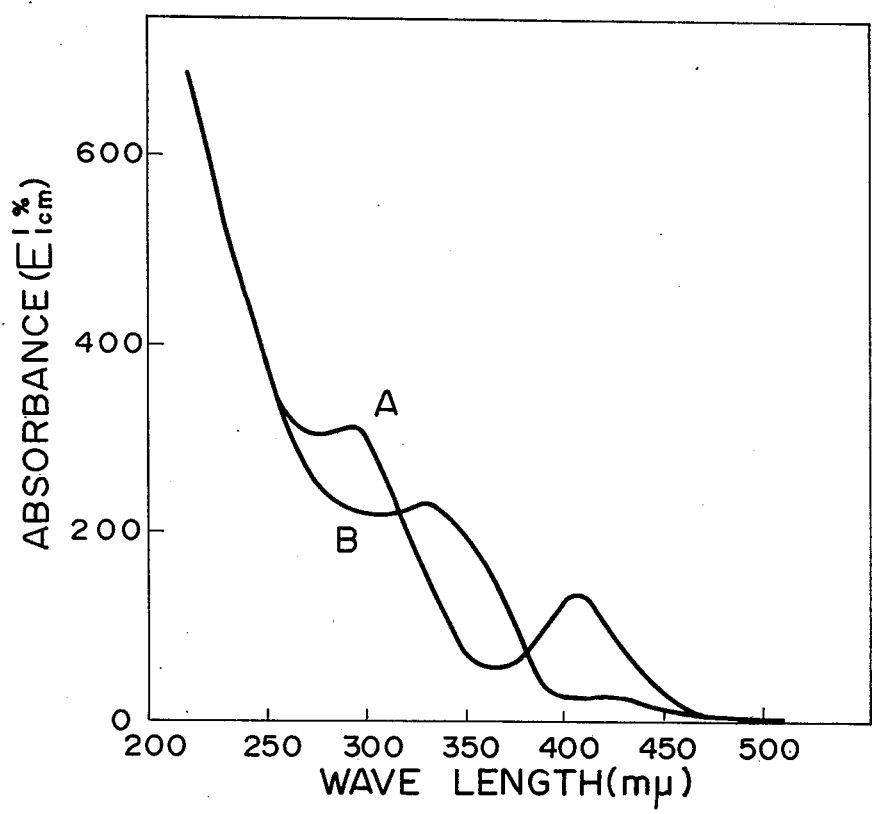
FIG. I

PROCESS FOR DECREASING AMMONIA CONCENTRATION IN DOMESTIC ANIMALS OR FOWLS

CROSS-REFERENCE TO RELATED APPLICATION

This application is a continuation-in-part of Application Ser. No. 32,253, filed Apr. 23, 1979, which in turn is a continuation of Ser. No. 830,773, filed Sept. 6, 1977, now abandoned, which is a continuation of Application Ser. No. 736,523, filed Oct. 28, 1976, now abandoned, which is a continuation-in-part of Application Ser. No. 681,198, filed Apr. 28, 1976, now abandoned.

BACKGROUND OF THE INVENTION

Heretofore antibiotics have been used in the medical treatment of the human body. Recently, the range of its use has expanded to include use as fungicides, growth promoting agents for animals, storage of industrial materials, preservation of foods etc.

In the case of animals, antibiotics have been given to them as a medicine or as a growth promoting agent. On the other hand, a method has been known for decreasing the offensive odor of the excrement of animals by giving them an enzyme, such as amylase or proteaze by mixing it into the animal feed.

This method effectuates a decrease of the offensive odor by action of the enzyme in the digestive mechanism of the animal body so treated. However, the health condition of the animals has considerable influence upon the action of the enzyme. This method does not always produce a definite effect, and the decrease of the offensive odor is limited only to the extent of 10% or less.

There has also been known a method for eliminating odor of the excrement of the animals by using the action of a deodorizing agent from outside, without recourse to the control of the interior mechanism inside the animal's body. However, this method produces only a limited degree of effect, since the deodorizing agent does not act directly on the substances causing the offensive odor.

Heretofore it has been known that acidophilus drinks or drugs, such as yogurt or Biofermin (trade mark) considerably improves the condition of the human body. More specifically, it has been known that such drinks or drugs control considerably the production of ammonia in the human body, especially in the intestines.

Animals, including human bodies, digest in their stomachs and intestines the protein they take, and decompose it into aminoacids which are absorbed into the intestine. Meanwhile, a part of the aminoacid is subjected to deamidization to produce ammonia. The ammonia produced enters into the blood, and is then converted in the liver into urea from which it is then excreted.

If it were possible to lower the ammonia concentration in intestine and blood, the state of health of animals would be considerably improved.

Hereupon, the inventors has found an antibiotic, multhiomycin, which lowers the ammonia concentration in the body of animals and, as a result, eliminates offensive odor in the excrement of animals, especially in the faeces of animals.

Multhiomycin is an antibiotic which was found in the soil of Japan by one of the inventors, Mr. Yonehara, and is disclosed in detail in the *Journal of Antibiotics* volume 23, No. 5, pp 231–237 (1970).

SUMMARY OF THE INVENTION

The object of the invention is to decrease the ammonia concentration in the interior of the body of domestic animals and fowls by giving them multhiomycin.

Another object of the invention is to improve their health condition by giving them multhiomycin.

A further object of the invention is to decrease the ammonia concentration in their excrement, especially faeces, by giving them multhiomycin.

Still another object of the invention is to improve the environment by decreasing the ammonia concentration in their excrement.

A still further object of the invention will become clear with reference to the following description.

Multhiomycin is not absorbed into the body of the animal given multhiomycin, and the total amount given is then completely excreted without even a small amount of it remaining in the body. Nevertheless, the intake of multhiomycin has a good influence in improving the digestive action of the digestive organs and produces a stabilizing effect by decreasing the ammonia concentration in the animal's body and excrements by $\frac{1}{2}$ or $\frac{1}{3}$ of the usual amount.

BRIEF DESCRIPTION OF THE DRAWING

FIG. 1 shows the ultraviolet absorption curves of multhiomycin in alkaline methanol (A) in neutral or acid methanol (B).

DETAILED DESCRIPTIONS OF THE PREFERRED EMBODIMENTS

Multhiomycin used in the invention is an antibiotic having the physical properties described hereunder, which is obtained by cultivating a multhiomycin producing strain belonging to the Genus Streptomyces in a broth to accumulate multhiomycin in the broth, extracting it from the broth and then purifying it.

Explaining briefly the process for producing multhiomycin, Streptomyces sp 8446 CCl (ATCC 31463) is inoculated into and cultivated in a culture medium comprising dextrine, dried yeast, sodium chloride, calcium carbonate etc., and then extraction of the culture medium with a solvent follows, and the extract is then purified by chromatography to obtain multhiomycin.

As seen from the Examples shown hereinafter, multhiomycin can decrease the ammonia concentration in the intestine and blood of the animals to the extent of $\frac{1}{3}$ to $\frac{1}{2}$ of the ammonia concentration of the animals in the untreated ordinary condition. At the same time, the amount of multhiomycin remaining in the internal organs or muscles of the treated animal is so little as to be not perceptible in a recognizable amount, while it displays a low degree of acute toxicity in comparison with other antibiotics. Therefore, multhiomycin can be used with a high degree of safety and it also make an excellent contribution to improving the health of the animals.

The reason seems to be that multhiomycin functions only in internal organs without being absorbed even a small amount into the interior of the animal body. This is shown by test results in vitro in which multhiomycin shows an astonishing action on bacteria, thus contributing to control of the generation of ammonia in the intestine and thus regulates the production of ammonia.

Furthermore, since multhiomycin prevents the generation of ammonia in the intestine of animals, the excrement of the treated animals contain very small amounts of ammonia as compared with the excrement of the untreated animals which have not been treated for the prevention of the occurrence of offensive odor. Therefore, multhiomycin significantly contributes to the improvement of the environment of or in the neighbourhood of a farm household which keep such animals.

As for the animals which can be treated according to the invention, these include domestic animals and fowls such as chickens, turkeys, cattle, pigs etc.

Administering multhiomycin to animals and fowls can be done by adding multhiomycin to the feed or drinking water. It is generally desirable to add to the feed or drinking water a drug previously prepared in the form of a liquid, emulsion or suspension etc. by mixing it in a harmless extender, diluent, solvent, or surfactant etc. In the case of adding multhiomycin to a feed stuff, it is convenient to prepare a pre-mixed composition which contains multhiomycin in amounts of 0.1 to 10% by weight in the feed stuff, and blend to a desired concentration with the feed stuff at the time of use.

Although the amounts of multhiomcyin added varies according to the animal and its stage of growth, it is generally used in an amount of about 0.1 to 500 ppm based on the weight of feed stuff or drinking water, and preferably about 0.5 to 100 ppm. Improved effects can be obtained by administering it in the form of finely divided particles having a size of 1 to 100$\mu$, preferably 5$\mu$ or less, to insure that the multhiomycin is not absorbed into the interior of the animal and fowl body.

In general, such finely ground multhiomycin is added in an amount of 0.5 to 100 g per ton of the feed stuff, or is added in an amount of 0.5 to 100 g of multhiomycin in the form of wettable powder to one liter of drinking water.

Multhiomycin is usable in the crude as well as purified form and fungus bodies containing multhiomycin are also usable.

As for the feed stuff to which multhiomycin is added in the form of a pre-feed or pre-composition, any feed stuff which is generally used for animals is suitable. For example, the said feed stuff can be corn, milo, soybean meal, alfalfa meal, soybean flour, lucern meal, fish meal, rice bran, wheat flour, wheat bran, fats or cottonseed meal. It is also possible to blend in other additives, for example, a surfactant or adjuvants such as sodium asparaginate, sorbitan monostearate, sorbitan monolaurate, Tween, calcium carbonate, sodium chloride, colin chloride and vitamins such as vitamin A, vitamin $B_1$, $B_2$, $B_6$ and $B_{12}$, vitamin D, vitamin E, calcium pantothenate, nicotinic acid amide, folic acid, inorganic salts such as iron sulfate, copper sulfate, magnesium sulfate, zinc sulfate, cobalt sulfate and amino acids, or other prophylactic medicines such as sulfa drugs, furan drugs, various kinds of coccidiostats and other antibiotics and antiparasites.

The antibiotic multhiomycin has the following physicochemical properties.

The elemental analysis of multhiomycin showed the following constituents: C 49.74; H 4.17; O 16.74; N 15.13 and S 15.03, and molecular weight measured by the vapor pressure method was 1064. It is believed from these facts that multhiomycin has the molecular formula, $C_{44}H_{45}O_{11}N_{11}S_5$. The melting point (decomposition point) of this antibiotic is higher than 300° C.

The ultraviolet adsorption curve of multhiomycin is as shown in the graph of FIG. 1. As seen from the graph, it shows a maximum absorptivity at 328 m$\mu$ ($E_1$ $cm^{1\%}$ 220) and 420 m$\mu$ ($E_1$ $cm^{1\%}$ 20) in the neutral or acid methanol (B), while in the alkaline methanol (A) it shows a maximum absorptivity at 292 m$\mu$ ($E_1$ $cm^{1\%}$ 255) and 406 m$\mu$ ($E_1$ $cm^{1\%}$ 132).

Multhiomycin is soluble in dimethylformamide, dimethyl sulfoxide and pyridine, but is only slightly soluble in ethyl acetate, methanol, ethanol and dioxane and is insoluble in water, acetic acid, n-hexane, ether, chloroform and many other organic solvents.

As for color reactions of multhiomycin, it develops various colors with ferric chloride reagent, Folin's reagent and Lemieux reagent, but it develops no color with ninhydrin reagent, Fehling's reagent and Ponceau-3R reagent or in the buret reactions.

Multhiomycin remains stable, when heated in an aqueous solution at 100° C. at a pH of 2 to 5 for five minutes. It is a slightly acidic and is in the form of yellow needle crystal. No optional activity is observed in its 1% solution.

The invention will be explained by way of Examples in the following for the sake of illustration without any intention of imposing limits on the invention and it must be understood that the invention is to be construed only on the basis of the appended claims.

EXAMPLE 1

Test on Ammonia Concentration in the Intestines of Multhiomycin-Administered Chickens Chickens just after hatching were divided into 5 groups, each consisting of 10 chickens. Diets containing 2.5 ppm or 5.00 ppm of multhiomycin were given to two groups, respectively, and diets containing 2.5 ppm or 5.00 ppm of thiopeptin were given to other two groups (comparative groups), respectively. A medicament-free diet was given to the remaining one group (control group). After 8 weeks, with respect to each group, the ammonia concentrations in the contents of the colon were determined according to a modification of the method of Fujii and Okuda, described hereinafter. The obtained results are shown in Table 1. The composition of the basal diet is shown in Table 2.

TABLE 1

| Influences of Multhiomycin and Thiopeptin on Ammonia Concentrations in Contents of Intestines | |
|---|---|
| Dietary Medicament | $NH_3$—N ($\mu$g/g of wet matter) Colon |
| Multhiomycin, 2.5 ppm | 60[b] |
| Multhiomycin, 5.0 ppm | 46[b] |
| Thiopeptin, 2.5 ppm | 120[a] |
| Thiopeptin, 5.0 ppm | 100[a] |
| None (control) | 155[a] |

Ammonia Concentration-Measuring Method (Modification of Fujii-Okuda Method)

A deproteinizing solution was added to the sample to deproteinize the sample and remove coloration-inhibiting components therefrom and simultaneously deactivate enzymes for preventing formation of ammonia during standing. The supernatant was separated and a coloring solution containing phenol and a nitroprusside salt was added thereto. Then, an alkaline solution was added to the mixture to make it alkaline, and a coloring solution containing sodium hypochlorite was further added to effect oxidation and form indophenol showing a blue color. The absorbance of this color at 630 m$\mu$ was measured to determine the ammonia nitrogen concentration. This measurement method is expressed by the following reaction formula:

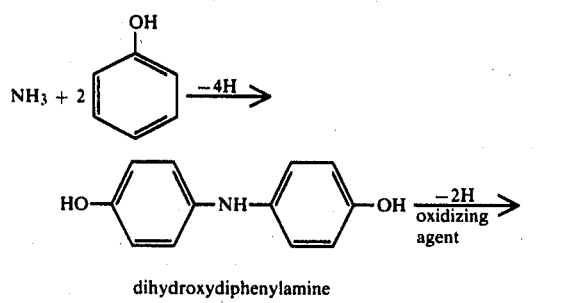

dihydroxydiphenylamine

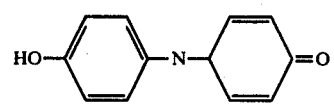

Incidentally, the nitroprusside salt acts as a catalyst in the above reaction.

TABLE 2

| Feed Materials | Composition of Basal Diet | |
|---|---|---|
| | Used in 0 to 4 Week Period | Used in 5 to Last Week Period |
| Corn | 49.5% | 52.0% |
| Soybean meal | 24.5% | 10.0% |
| Milo | 12.2% | 14.5% |
| Fats | — | 7.0% |
| Lucerne meal | 4.0% | 3.5% |
| Fish meal | 6.5% | 9.8% |
| Sodium chloride | 0.3% | 0.2% |
| Calcium carbonate | 1.5% | 1.5% |
| Calcium phosphate | 1.0% | 1.0% |
| Premix* | 0.5% | 0.5% |
| Coccidium preventive (Amprolium) | 125 ppm | 125 ppm |

*The premix contains vitamin A, vitamin $D_3$, vitamin E, vitamin $B_1$, vitamin $B_2$, vitamin $B_6$, vitamin $B_{12}$, pantothenic acid, nicotinic acid, choline chloride, folic acid, iron sulfate, copper sulfate, cobalt and zinc.

EXAMPLE 2

Test on Ammonia Concentration in Portal Blood in Multhiomycin-Administered Pigs Young pigs just after weaning were divided into 3 groups, each consisting of 6 pigs. Diets containing 10 ppm of multhiomycin were given to one group, diets containing 10 ppm of thiopeptin as the comparative medicament were given to another group, and a medicament-free diet was given to the remaining one group (control group). After 2 months, with respect to each group, the ammonia concentrations in portal blood were determined according to the modified Fujii-Okuda method. The obtained results are shown in Table 3. The composition of the basal diet is as shown in Table 4.

TABLE 3

| Influences of Multhiomycin and Thiopeptin on Ammonia Concentrations in Portal Blood | |
|---|---|
| Dietary Medicament | $NH_3$—N (μg/ml) Portal Blood |
| Multhiomycin, 10 ppm | $3.44^c$ (−3.36) |
| Thiopeptin, 10 ppm | $6.00^b$ (−0.8) |
| None (control) | $6.80^a$ (—) |

TABLE 4

| Feed Materials | Composition of Basal Diet | |
|---|---|---|
| | Initial Stage | Final Stage |
| Corn | 50.0% | 50.0% |
| Defatted rice bran | 13.0% | 13.0% |
| Wheat bran | 9.2% | 9.1% |
| Barley bran | 12.0% | 17.0% |
| Soybean meal | 6.0% | 3.0% |
| Fish meal (CP 65%) | 3.0% | 1.0% |
| Lucerne meal | 5.0% | 5.0% |
| Calcium carbonate | 0.8% | 0.9% |
| Sodium chloride | 0.5% | 0.5% |
| Premix* | 0.5% | 0.5% |

*The premix was the same as that shown in Table 2.

EXAMPLE 3

Ammonia Concentration Test in the Excrement of Chickens to which Multhiomycin was Administered The tests were made on commercially available chickens for exclusive use as broilers (kind: Hubbard). 150 Chickens which were just hatched (male: 75, female: 75) were divided into 3 groups, each consisting of 50 chickens. Basal diets (containing no antibiotics, see Tables 6 and 7) were given to one group, and diets containing 2.5 ppm or 10 ppm of multhiomycin were given to the other two groups. The feed was constantly supplied to each group with water for 8 weeks from the hatching. Each group was bred in one windless cage (1.8×5.4×2.7 m, 9.7 m² per group), and each cage was kept warm by circulating warm water under the floor until the chickens were two weeks old. Further, the floor were covered with wood chips in a depth of about 3 cm.

About 6 or 8 weeks from the beginning of the test, the ammonia concentration in excrement was measured in each group. The ammonia concentrations in the excrement were measured with Kitagawa's vacuum gas detector and the moisture content therein was measured with the hot-air drying method whereby 2 kg weight of excrement (containing chips) was treated at 100°±2° C. for 24 hours to measure its moisture content. The obtained results are shown in Table 5.

TABLE 5

| | Ammonia Concentration (ppm) in Excrement | |
|---|---|---|
| | Weeks of Age | |
| Group | 6 weeks | 8 weeks |
| 1. Control (no addition) | 25.5 | 29.7 |
| 2. Group Fed with 2.5 ppm of Multhiomycin | 9.8 | 11.2 |
| 3. Group Fed with 10 ppm of Multhiomycin | 9.0 | 10.0 |

TABLE 6

| | Composition of Basal Diets | |
|---|---|---|
| | % | |
| Ingredients | 0–4 weeks | 5–8 weeks |
| Yellow corn | 42.6 | 42.0 |
| Milo meal | 19.5 | 20.6 |
| Soybean meal | 19.0 | 8.0 |
| Sesame meal | 4.0 | 4.0 |
| Fish meal (65% CP) | 6.0 | 9.5 |
| Fish soluble (45% CP) | 2.6 | 2.4 |
| Calcium carbonate | 1.4 | 1.3 |
| Fat feed | — | 7.0 |
| Rusan meal | 2.0 | 2.0 |
| Calcium phosphate | 1.2 | 1.2 |

TABLE 6-continued

| Composition of Basal Diets | | |
|---|---|---|
| | % | |
| Ingredients | 0–4 weeks | 5–8 weeks |
| Mycelium | 0.5 | 0.5 |
| Salt | 0.2 | — |
| Premix | 1.0 | 0.5 |
| Total[1] | 100.0 | 100.0 |

[1]Containing amprolium 125 ppm, ethopobate 8 ppm due to coccidiostat.

TABLE 7

| Composition of Premix | |
|---|---|
| Ingredients | Per Kg |
| Vitamin A | 2,400,000 IU |
| Vitamin $D_3$ | 480,000 IU |
| Vitamin E | 100 IU |
| Vitamin $B_1$ | 400 mg |
| Vitamin $B_2$ | 2,400 mg |
| Vitamin $B_6$ | 800 mg |
| Calcium pantothenate | 3,600 mg |
| Nicotinic acid | 5,600 mg |
| Choline chloride | 120,000 mg |
| Folic acid | 40 mg |
| Magnesium | 48,000 mg |
| Iron | 8,000 mg |
| Copper | 800 mg |
| Iodine | 400 mg |
| Cobalt | 40 mg |
| Zinc | 32,000 mg |

EXAMPLE 4

Test on the Amounts of Multhiomycin Remaining in the Interior of the Chicken's Bodies After giving the broilers multhiomycin for 10 weeks in an increased amount of 400 to 3,200 times the amounts in the usually used concentration (2.5 ppm), the remaining amounts of multhiomycin in the blood sera, muscles and main organs of the treated chickens were measured.

40 Chickens exclusively used as broilers (kind: Hubbard) were divided into 5 groups. A diet containing no multhiomycin was given to one group, and diets containing 1,000, 2,000, 4,000 and 8,000 ppm of multhiomycin were given to the other four groups respectively for 10 weeks from just after hatching. The remaining amounts of multhiomycin in the blood sera, breast muscles, livers, kidneys and spleens of the treated chickens were determined according to the microbial quantitative method.

The obtained results are shown in Table 8. No multhiomycin was detected in the main organs (liver, kidney and spleen) and edible parts (breast muscle), that is to say the amount remaining thereof was below the detecting limit of 50 ppb in sera, and 10 ppb in main organs.

TABLE 8

| Multhiomycin Concentration | Detected Parts ($\mu$g/ml or g) | | | | |
|---|---|---|---|---|---|
| | Serum | Breast Muscle | Liver | Kidney | Spleen |
| 0 | ND | ND | ND | ND | ND |
| 1,000 | ND | ND | ND | ND | ND |
| 2,000 | ND | ND | ND | ND | ND |
| 4,000 | ND | ND | ND | ND | ND |
| 8,000 | ND | ND | ND | ND | ND |

ND means not-detected.

EXAMPLE 5

Influence on Environment

The rise and fall in the activity of the multhiomycin excreted without absorption in the interior of the animal body was compared with the activity of other antibiotics, such as thiopeptin and thiostrepton.

(1) Rise and fall in the activity of antibiotics in the excrement

Multhiomycin, thiopeptin and thiostrepton were respectively added to the excrement of chickens bred with the feed containing no antibiotics in a concentration of 10 $\mu$g/g. The excrement was preserved under room temperature condition and the remaining potency of each antibiotic in excrement was measured at different time intervals with a microbal quantitative method.

The results obtained are shown in Table 9. As seen from Table 9, the remaining multhiomycin after 5 days was below that of the detectable limit of the measuring method, but the remaining ratios of thiopeptin and thiostrepton were respectively 52% and 43%.

TABLE 9

| Remaining Amounts of each Antibiotics in the Excrement of Chickens | |
|---|---|
| Chemicals | Remaining amounts after 5 days |
| Multhiomycin | 0 |
| Thiopeptin | 52% |
| Thiostrepton | 43% |

(2) Behavior of the antibiotics in soil

To soils (collected in Kikukawa-cho, Ogasa-gun, Shizuoka-ken, Japan) which were confirmed to have no anti-antibiotic activity were respectively added multhiomycin, thiopeptin and thiostrepton, each containing 10 $\mu$g/g concentration of each antibiotic. The soils were preserved under room temperature condition, and the remaining potencies in soils of each antibiotic were measured at different time intervals according to the microbal quantitative method.

The results obtained are shown in Table 10. As seen from the Table, the amount of multhiomycin remaining after 60 days was 0, but those of thiopeptin and thiostrepton were respectively 41% and 44%.

TABLE 10

| Behavior of Antibiotics in Soil | |
|---|---|
| Chemicals | Remaining Ratio after 60 Days |
| Multhiomycin | 0 |
| Thiopeptin | 41% |
| Thiostrepton | 44% |

EXAMPLE 6

Acute toxicity

Acute toxins of multhiomycin, thiopeptin and thiostrepton administered to mice, were measured by injection of each drug into the abdominal cavities of the mice. The results are shown in Table 11. The administering multhiomycin to mice in amounts of 4,000 mg/kg did not cause a single death.

On the contrary, thiopeptin and thiostrepton show small values of $LD_{50}$ as shown in the Table.

TABLE 11

| Chemicals | Acute Toxicity (LD$_{50}$ mg/kg) | |
| --- | --- | --- |
| | Male Mouse | Female Mouse |
| Multhiomycin | >4,000 | >4,000 |
| Thiopeptin | 780 | 660 |
| Thiostrepton | 85 | — |

What we claim is:

1. A process for decreasing the ammonia concentration in the interior of the body of an animal or fowl and in the excrement of said animal or fowl which comprises administering an ammonia reducing effective amount of multhiomycin to said animal or fowl by giving to said animal or fowl a feed and/or drinking water containing multhiomycin.

2. A process according to claim 1 wherein said animal or fowl comprises chickens, turkeys, pigs and cattle.

3. A process according to claim 1 wherein multhiomycin is given to said animal or fowl in a concentration of 0.1 to 500 ppm.

4. A process according to claim 1, wherein multhiomycin is in the form of finely ground particles having a particle size of 1 to 100μ.